US00PP31490P2

(12) United States Plant Patent
Hansen

(10) Patent No.: US PP31,490 P2
(45) Date of Patent: Feb. 25, 2020

(54) **X *MANGAVE* PLANT NAMED 'MY DOG SPOT'**

(50) Latin Name: **x *Mangave* times x *Mangave* hybrid**
Varietal Denomination: My Dog Spot

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,921

(22) Filed: Feb. 1, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique cultivar of X *Mangave* plant named 'My Dog Spot' characterized by compact, low-growing habit and lanceolate foliage with medium green color and with high ultra violet light exposure developing burgundy speckling on light green to chartreuse leaves. The yellowish to chartreuse flowers on tall stiff scapes are loaded with nectar for attracting hummingbirds. The new plant is suitable as a patio or container plant, for the garden or for use as a houseplant.

1 Drawing Sheet

Botanical classification: x *Mangave* times x *Mangave* hybrid.
Variety denomination: 'My Dog Spot'.

STATEMENT REGARDING PRIOR DISCLOSURES UNDER 37 CFR 1.77(b)(6)

The first public disclosure of the claimed plant, in the form of a photograph and brief description on a website operated by Walters Gardens, Inc. on Feb. 1, 2018. The claimed plant was first sold on Mar. 12, 2018 by Walters Gardens, Inc., who obtained the plant and all information relating thereto, from the inventor. No plants of x *Mangave* 'My Dog Spot' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct X *Mangave* plant, X *Mangave* 'My Dog Spot' hybridized on Apr. 17, 2014 by the inventor at a wholesale perennial nursery in Zeeland, Mich., USA as a cross between an unreleased proprietary hybrid known by the breeder code H10-02 as the female or seed parent and an unreleased proprietary hybrid known by the breeder code 12-06-01 as the male or pollen parent. Through trials at the same nursery the plant was referred to by the code 14-18-2. The new plant has been successfully asexually propagated initially in 2016 by division at the same nursery in Zeeland, Mich. and also by tissue culture. Both methods of asexual propagation systems have been found to produce stable and identical plants that maintain all the unique characteristics of the original plant in successive generations.

BRIEF SUMMARY OF THE INVENTION

X *Mangave* 'My Dog Spot' differs from its parents as well as all other *Manfreda, Agave* and X *Mangave* known to the applicant. The most similar known X *Mangave* cultivar known to the inventor are: 'Spotty Dotty' U.S. Plant Pat. No. 29,917, 'Inkblot' U.S. Plant Pat. No. 29,431, 'Freckles and Speckles' U.S. Plant Pat. No. 30,904, and 'Bloodspot' (not patented).

'Spotty Dotty' is a larger plant and has significantly broader, greater number and more green leaves with smaller spots of purple, blushing in high light intensity and a slightly more wavy leaf. 'Inkblot' has leaves that are broader and arch more, with larger spots and a more greyed-purple coloration to the leaf and the flowers are burgundy colored and not the yellowish flowers of 'My Dog Spot'. 'Freckles and Speckles' is larger in habit with broader, more ovate-shaped and thicker leaves, the leaf color is more greyed-purple and the flowers are darker with more burnt-orange hue blushing on the tepals. 'Bloodspot' is more upright in habit with more leaves per plant that are more ovate-shaped the terminal and marginal spines are larger and darker reddish colored. The female parent has bright yellow flowers on heavier branched scapes and the foliage is more silvery, broader and more wavy than the new plant. The male parent has flatter habit, a non-branched scape with mahogany flowers, the foliage is more silver with fewer but larger burgundy spots, and foliage is broader than the new plant.

The new plant, 'My Dog Spot', is unique from all of these variegated *Agave*, X *Mangave* and *Manfreda* known to the inventor by the following combined traits:

1. Compact, low-growing habit with 30 to 45 leaves at flowering;
2. Foliage lanceolate with small flexible marginal teeth;
3. Foliage develops burgundy speckling throughout on light green to chartreuse leaves;
4. Moderate to rapid growth rate with good natural pup production;
5. Yellowish to chartreuse flowers on stiff, upright, non-branched scapes.

BRIEF DESCRIPTION OF THE DRAWINGS

The photograph of the new plant demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
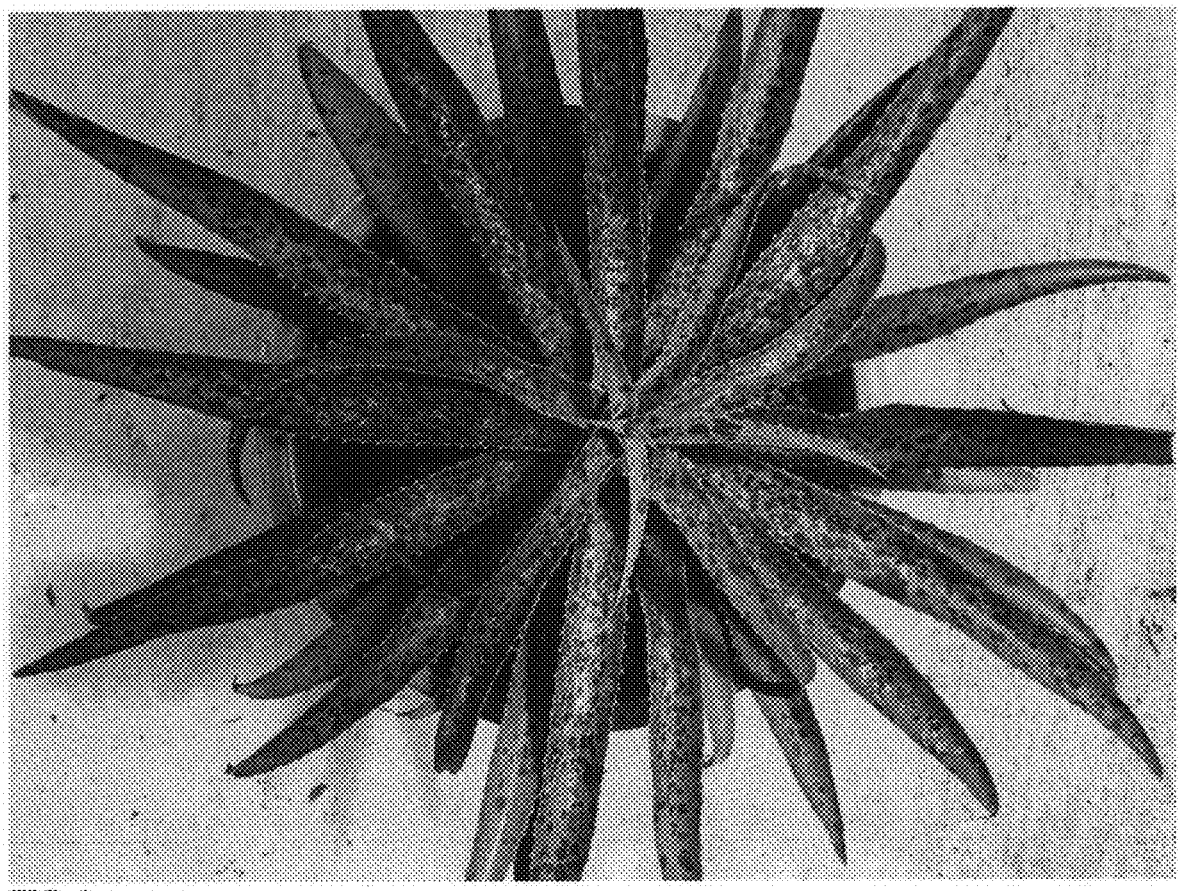
FIG. 1 shows the new plant in a container showing foliage and base of scape.
Figure 2:
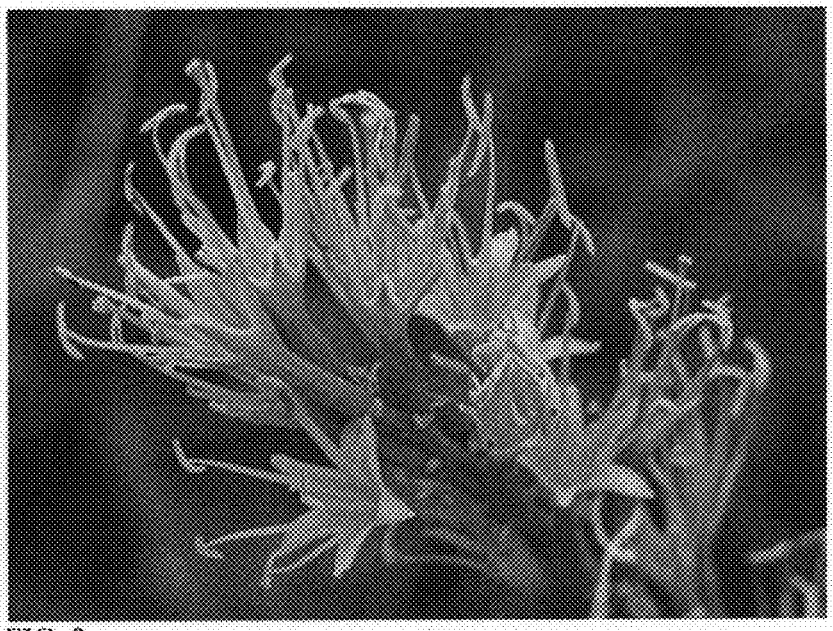
FIG. 2 shows a close-up of the flowers and buds in the upper scape.

The following descriptions and color references are based on the 2015 edition of The Royal Horticultural Society Colour Chart except where common dictionary terms are used. The new plant, X *Mangave* 'My Dog Spot', has not been observed under all possible environments. The phenotype may vary slightly with different environmental conditions, such as temperature, light, fertility, moisture and maturity levels, but without any change in the genotype. The following observations and size descriptions are of two and three-year old plants in a commercial wholesale greenhouse in Zeeland, Mich. with supplemental water and fertilizer as needed.

Botanical classification: X *Mangave* hybrid;

Parentage: H10-02 as the female or seed parent, which is a proprietary unnamed selection of *Manfreda maculosa* times a unnamed selection of *Agave geminflora*; and 12-06-01 as the male or pollen parent, which is a cross between 'Bloodspot' times a unnamed unique selection of *Agave geminflora;*

Propagation: Division and sterile plant tissue culture;

Time to initiate roots from tissue culture: About 21 days;

Growth rate: Moderate to rapid;

Crop time: About 12 to 16 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of up to about 40 fleshy leaves radially emerging and arching from central rhizome, producing a symmetrical rounded mound;

Plant size: Foliage height about 20.0 cm tall from soil line to the top of the leaves, flowering to about 90.0 cm tall and about foliage to about 40.0 cm wide at the widest point at soil line;

Foliage description: Lanceolate; simple, fleshy, glabrous; margins finely dentate with flexible teeth; apex acute with flexible mucro; base truncate, sessile, clasping;

Leaf size: To about 21.5 cm long, about 22.0 mm wide at base and 5.0 mm thick, average about 20.0 cm long, 16.0 mm wide and 4.5 mm thick; typically bi-laterally symmetrical; glabrous and slightly glaucous above and below; spots of variable sizes from about 0.5 mm diameter to about 10.0 mm long and 5.0 mm across; teeth about 1.0 mm to 2.0 mm long, about 2.0 mm across at base and 4.0 to 5.0 mm apart;

Foliage fragrance: None observed;

Leaf blade color:

*Adaxial* (*young*).—Nearest RHS 138B with speckles between RHS N186B or RHS 137B in lower light.

*Abaxial* (*young*).—Nearest RHS 138C with speckles nearest RHS 137B.

*Adaxial* (*mature*).—Between RHS 148D and N 148D, maculate with spots of nearest RHS; N187A and with higher ultraviolet exposure blushed with nearest RHS N186C.

*Abaxial* (*mature*).—Nearest RHS 146D near midrib and distally becoming nearest RHS 148C with speckles of variable color, some nearest RHS N187A and others nearest RHS 137B and others nearest RHS 138B.

*Teeth*.—Adaxial and abaxial nearest RHS NN155C.

Apical mucro: Flexible; straight, about 5.0 mm long;

Apical mucro color: Nearest RHS 176B;

Apical mucro texture: Flexible, glabrous, sharply pointed; about 1.5 cm long and 2.5 mm across at base;

Petiole: Sessile;

Veins: Parallel; not distinct;

Peduncle: Cylindrical; glaucous; glabrous; stiff; strong; non-branched; about 90.0 cm long and 10.0 mm diameter at base and 6.0 mm diameter below first flowers; flowering portion about 38.0 cm tall and about 8.0 cm across; attitude upright;

Peduncle color: Basal portion before flowers nearest RHS N187A, flowering portion nearest RHS 138A;

Pedicel: Cylindrical; glaucous; glabrous; stiff; strong; average about 10.5 mm long and 2.2 mm diameter;

Pedicel color: Nearest RHS 138A;

Cauline leaves: About 18 per scape; lanceolate; simple, fleshy, glabrous; margins finely dentate with flexible teeth; apex narrowly acute with flexible mucro; base truncate, sessile, clasping; proximally about 12.0 cm long and about 10.0 mm wide at base, decreasing distally; color adaxial and abaxial same as basal leaves;

Buds one day prior to opening: Elongated globose; about 3.6 cm long and about 7.0 mm across at mid-tepal, base about 4.0 mm diameter;

Bud color: Nearest RHS 138A in basal portion and distally becoming nearest RHS 160C;

Flower description: Perfect, actinomorphic; about 9.2 cm long and opening to about 2.6 cm across at outside of anthers; lasting about 3 to 4 days per flower; flowering period about two weeks in late winter in Michigan greenhouse; producing abundant nectar; approximately 28 flowers per scape; attitude mostly upright;

Flower fragrance: Faintly sweet;

Tepals: Six in two sets of three; glaucous abaxial and slightly lustrous adaxial; glabrous both adaxial and abaxial; acute apex and fused base; outer set about 4.8 cm long, fused in basal 4.2 cm and about 5.0 mm wide at base; inner set about 4.8 cm long and 6.0 mm wide at fusion; inner set creased along edge where overlapped with outer set while in bud;

Tepal color: Adaxial outer and inner tepal set base nearest RHS 1D with center midrib between RHS 145A and RHS 145B; abaxial outer set base between RHS 146D and RHS 145A with distal non-fused portion nearest RHS 161B, abaxial inner set base between RHS 146D and RHS 145A, margin nearest RHS 2D and center nearest RHS 161C;

Androecium: Six;

*Filaments*.—Six; cylindrical distally, slightly applanate base; stiff and straight; about 3.3 cm long and 1.0 mm diameter at base; color between RHS 145A and RHS 145B.

*Anther*.—Dorsifixed; longitudinal; about 1.3 cm long and 1.5 mm diameter before opening; after dehiscence curving backward; color nearest RHS 163A.

*Pollen*.—Abundant; color nearest RHS 1A.

Gynoecium: Single; 4.6 cm long;

*Style*.—3.5 cm long and 2.0 mm diameter at base; color nearest RHS 162C.

*Stigma*.—Turbinate, apex tri-lobed; about 2.5 mm tall and 3.5 mm across top; color base nearest RHS 183C; top stigmatic surface in tri-pointed star with color nearest NN155B.

*Ovary*.—Inferior.

Fruit: Dehiscent, tri-valved, loculicidal capsule; apex abruptly acute; base slightly tapered; about 2.7 cm long and 1.2 cm across;

Fruit color: When immature nearest RHS N138A; at dehiscence blend between RHS 199C and RHS N199B;

Seed: Flattened, near round; about 5.0 mm long 3.0 mm across and about 1.0 mm thick; color blend between RHS N200A and RHS 202A;

Disease resistance: X *Mangave* 'My Dog Spot' has not been observed to be susceptible or resistant to diseases common to other X *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental X *Mangave* plant named 'My Dog Spot' as herein described and illustrated.

* * * * *